(12) United States Patent
Houser et al.

(10) Patent No.: US 10,010,341 B2
(45) Date of Patent: *Jul. 3, 2018

(54) ULTRASONIC SURGICAL SHEARS AND METHOD FOR SEALING A BLOOD VESSEL USING SAME

(71) Applicant: Ethicon LLC, Guaynabo, PR (US)

(72) Inventors: Kevin L. Houser, Springboro, OH (US); Sarah A. Noschang, Mason, OH (US)

(73) Assignee: Ethicon LLC, Los Frailes Industrial Park Guaynabo, PR (US)

( * ) Notice: Subject to any disclaimer, the term of this patent is extended or adjusted under 35 U.S.C. 154(b) by 95 days.

This patent is subject to a terminal disclaimer.

(21) Appl. No.: 14/829,116

(22) Filed: Aug. 18, 2015

(65) Prior Publication Data

US 2015/0351792 A1 Dec. 10, 2015

Related U.S. Application Data

(63) Continuation of application No. 13/896,380, filed on May 17, 2013, now Pat. No. 9,168,055, which is a (Continued)

(51) Int. Cl.
*A61B 17/32* (2006.01)
*A61B 17/12* (2006.01)
*A61B 17/28* (2006.01)

(52) U.S. Cl.
CPC ...... *A61B 17/320092* (2013.01); *A61B 17/12* (2013.01); *A61B 2017/2825* (2013.01); *A61B 2017/320094* (2017.08)

(58) Field of Classification Search
CPC .... A61B 17/320068; A61B 17/320092; A61B 2017/2825

See application file for complete search history.

(56) References Cited

U.S. PATENT DOCUMENTS 3,636,943 A * 1/1972 Balamuth .............. A61B 17/11
156/73.3
3,862,630 A * 1/1975 Balamuth .............. A61B 17/11
606/1
(Continued)

FOREIGN PATENT DOCUMENTS

EP 0908152 B1 1/2002
EP 1362555 B1 6/2005
(Continued)

OTHER PUBLICATIONS

Emam, Tarek et al., "How Safe is High-Power Ultrasonic Dissection?," Annals of Surgery 2003, 186-191 pp., vol. 237, No. 2, Lippincott Williams & Wilkins, Inc. 2003, Philadelphia, PA.
(Continued)

*Primary Examiner* — Ryan J Severson
(74) *Attorney, Agent, or Firm* — Verne E. Kreger, Jr.

(57) ABSTRACT

An ultrasonic surgical shears includes an ultrasonic surgical blade, a clamping arm operable to open and close toward the blade, and a tissue pad attached to the clamping arm. A method for sealing a blood vessel of a patient includes obtaining an ultrasonic surgical shears and positioning the blood vessel between the blade and the tissue pad. The clamping arm is operated to exert an average coaptation pressure between and including 120 psi and 210 psi. The blade is ultrasonically vibrated to transect and seal the blood vessel.

12 Claims, 9 Drawing Sheets

Related U.S. Application Data continuation of application No. 13/462,946, filed on May 3, 2012, now Pat. No. 8,460,326, which is a continuation of application No. 11/065,671, filed on Feb. 24, 2005, now Pat. No. 8,182,501.

(60) Provisional application No. 60/548,308, filed on Feb. 27, 2004.

(56) References Cited

U.S. PATENT DOCUMENTS

| | | | |
|---|---|---|---|
| 5,322,055 A | | 6/1994 | Davison et al. |
| 5,383,883 A | * | 1/1995 | Wilk ................ A61B 17/12013 604/22 |
| 5,776,130 A | | 7/1998 | Buysse et al. |
| 5,873,873 A | * | 2/1999 | Smith ............ A61B 17/320092 606/1 |
| 5,944,737 A | * | 8/1999 | Tsonton ......... A61B 17/320092 604/22 |
| 5,947,984 A | | 9/1999 | Whipple |
| 6,024,750 A | | 2/2000 | Mastri et al. |
| 6,036,667 A | * | 3/2000 | Manna ........... A61B 17/320092 604/22 |
| 6,063,050 A | | 5/2000 | Manna et al. |
| 6,066,151 A | * | 5/2000 | Miyawaki ...... A61B 17/320068 606/169 |
| 6,129,735 A | * | 10/2000 | Okada ............ A61B 17/320068 606/169 |
| 6,187,003 B1 | | 2/2001 | Buysse et al. |
| 6,254,623 B1 | | 7/2001 | Haibel, Jr. et al. |
| 6,325,811 B1 | | 12/2001 | Messerly |
| 6,340,352 B1 | * | 1/2002 | Okada ............ A61B 17/320092 601/2 |
| 6,352,532 B1 | | 3/2002 | Kramer et al. |
| H002037 H | * | 7/2002 | Yates ............... A61B 17/07207 606/51 |
| H2037 H | | 7/2002 | Yates et al. |
| 6,458,142 B1 | | 10/2002 | Faller et al. |
| 6,468,286 B2 | * | 10/2002 | Mastri .................... A61B 17/29 606/169 |
| 6,669,690 B1 | | 12/2003 | Okada et al. |
| 6,869,439 B2 | * | 3/2005 | White ............ A61B 17/320092 606/169 |
| 7,131,983 B2 | | 11/2006 | Murakami |
| 7,156,846 B2 | | 1/2007 | Dycus et al. |
| 7,361,172 B2 | | 4/2008 | Cimino |
| 8,182,501 B2 | | 5/2012 | Houser et al. |
| 8,444,663 B2 | * | 5/2013 | Houser ........... A61B 17/320092 606/169 |
| 8,460,326 B2 | | 6/2013 | Houser et al. |
| 9,168,055 B2 | * | 10/2015 | Houser ................. A61B 17/12 |
| 2001/0025184 A1 | * | 9/2001 | Messerly ....... A61B 17/320092 606/169 |
| 2002/0002379 A1 | * | 1/2002 | Bishop ........... A61B 17/320092 606/169 |
| 2002/0026184 A1 | | 2/2002 | Witt et al. |
| 2002/0120306 A1 | | 8/2002 | Zhu et al. |
| 2002/0183785 A1 | | 12/2002 | Howell et al. |
| 2003/0114851 A1 | * | 6/2003 | Truckai ............. A61B 18/1445 606/51 |
| 2003/0114874 A1 | | 6/2003 | Craig et al. |
| 2003/0120306 A1 | | 6/2003 | Burbank et al. |
| 2005/0192610 A1 | * | 9/2005 | Houser ........... A61B 17/320092 606/169 |
| 2005/0192612 A1 | * | 9/2005 | Houser ................. A61B 17/12 606/169 |
| 2006/0030848 A1 | * | 2/2006 | Craig ............ A61B 17/320092 606/49 |
| 2010/0023044 A1 | * | 1/2010 | Houser ........... A61B 17/320092 606/169 |
| 2012/0215244 A1 | * | 8/2012 | Houser ................. A61B 17/12 606/169 |
| 2013/0253558 A1 | * | 9/2013 | Houser ................. A61B 17/12 606/169 |
| 2015/0351792 A1 | * | 12/2015 | Houser ................. A61B 17/12 606/171 |

FOREIGN PATENT DOCUMENTS

| | | |
|---|---|---|
| JP | 8-503621 T | 4/1996 |
| JP | 11-197157 A | 7/1999 |
| JP | 2000-139943 A | 5/2000 |
| JP | 2000-210296 A | 8/2000 |
| JP | 2001-198137 A | 8/2000 |
| WO | WO 01/24713 A1 | 4/2001 |

OTHER PUBLICATIONS

Feil, Wolfgang, MD et al.; Ultrasonic Energy for Cutting, Coagulating, and Dissecting; p. IV, 17, 21, 23; ISBN 3-13-127521-9 (New York, NY, Thieme New York, 2005).

McCarus, Steven D., MD; Physiologic Mechanism of the Ultrasonically Activated Scalpel; Journal of the American Ass'n of Gynecologic Laparoscopists; Aug. 1996; vol. 3 No. 4 p. 601ff.

Procedural Letter from the European Patent Office dated Apr. 7, 2011; Application No. 05723929.5.

European Office Action dated Jun. 21, 2010; Application No. 05723929.5.

Response to European Office Action dated Jun. 14, 2011; Application No. 05723929.5.

Order Granting Defendants' Motion for Summary Judgment of Non-Infringement and Invalidity of U.S. Pat. No. 8,182,501 (Doc. 103); Judge Timothy S. Black; Filed Jan. 22, 2014; Case No. 1:11-cv-871; 58 pgs.

Order Denying Defendants' Motion for Summary Judgment of Unenforceability of U.S. Pat. No. 8,182,501 for Inequitable Conduct (Doc. 106); Judge Timothy S. Black; Filed Jan. 22, 2014; Case No. 1:11-cv-871; 23 pgs.

International Search Report dated Sep. 5, 2007; International Application No. PCT/US2005/006273.

European Search Report dated Sep. 25, 2009; Application No. 05723929.5.

United States Court of Appeals for the Federal Circuit—Notice of Entry of Judgment Accompanied by Opinion (U.S. Pat. No. 8,182,501) (Docs. 69-1 thru 69-4); Judges Lourie, Bryson, and Chen; Filed Aug. 7, 2015; Case No. 14/1370; 47 pgs. (Appeal of Case No. 1:11-cv-871 Judge Timothy S. Black).

* cited by examiner

ULTRASONIC SURGICAL SHEARS AND METHOD FOR SEALING A BLOOD VESSEL USING SAME

REFERENCE TO RELATED APPLICATIONS

The present application is a continuation of U.S. patent Ser. No. 13/896,380, filed on May 17, 2013, now U.S. Pat. No. 9,168,055, which is a continuation of U.S. patent Ser. No. 13/462,946, filed on May 3, 2012, now U.S. Pat. No. 8,460,326, which is a continuation of U.S. patent Ser. No. 11/065,671 filed Feb. 24, 2005, now U.S. Pat. No. 8,182,501, which claims the priority benefit of U.S. provisional patent application Ser. No. 60/548,308, filed on Feb. 27, 2004, wherein the contents of all applications are incorporated herein by reference.

This application contains subject matter related to co-owned patent application Ser. No. 10/289,787, filed on Nov. 7, 2002, entitled "Ultrasonic Clamp Coagulator Apparatus Having an Improved Clamping End-Effector", United States Pub. 2003/0114874, the contents of which is incorporated herein by reference.

FIELD OF THE INVENTION

The present invention is related generally to surgical instruments, and more particularly to an ultrasonic surgical shears and to a method for sealing a blood vessel using an ultrasonic surgical shears.

BACKGROUND OF THE INVENTION

Ultrasonic surgical instruments are known which include ultrasonic surgical shears having an ultrasonic surgical blade, a clamping arm operable to open and close toward the blade, a tissue pad attached to the clamping arm and including a 0.033 square-inch clamping surface area, and a device for exerting a 1.5 pound clamping force on the clamping arm which creates a clamping pressure of 45 psi (pounds per square inch) on a blood vessel which is positioned between the clamping surface area of the tissue pad and the blade. It is noted that the clamping surface area is the area where the blade and the tissue pad are in close proximity when the clamping arm is in a closed position. Exemplary devices are described in U.S. Pat. Nos. 5,322,055 and 6,325,811, the contents of which are incorporated herein by reference. The result of the ultrasonically-vibrating ultrasonic surgical blade and the clamping pressure on the blood vessel is a coaptation of the blood vessel (a bringing together of the walls of the blood vessel), a transection (a cutting) of the coaptated blood vessel, and a coagulation (a sealing) of the coaptated cut ends of the blood vessel. It is known that blood-vessel transection times can be decreased with the application of a higher clamping force. However, this is not done because conventional thought is that decreasing the blood-vessel transection time using a higher clamping force will lead to a degradation in coagulation performance (i.e., a lowering of the burst pressure of a sealed end of the transected blood vessel). Conventional ultrasonic surgical shears are not used on blood vessels larger than 3 mm because the clamping force used is inadequate for proper coaptation.

Still, there is a need in the medical device industry for improved ultrasonic surgical shears and improved methods for sealing a blood vessel using an ultrasonic surgical shears.

SUMMARY OF THE INVENTION

A first method of the invention is for sealing a blood vessel of a patient and includes steps a) through d). Step a) includes obtaining an ultrasonic surgical shears including an ultrasonic surgical blade, a clamping arm operable to open and close toward the blade, and a tissue pad attached to the clamping arm. Step b) includes positioning the blood vessel between the blade and the tissue pad. Step c) includes operating the clamping arm to exert an average coaptation pressure on the blood vessel between and including 60 psi and 210 psi. Step d) includes ultrasonically vibrating the blade to transect and seal the blood vessel.

A first embodiment of the invention is for an ultrasonic surgical shears including an ultrasonic surgical blade, a clamping arm, and a tissue pad. The clamping arm is operable to open and close toward the blade. The tissue pad is attached to the clamping arm. The ultrasonic surgical shears also includes a device for exerting a clamping force on the clamping arm creating an average clamping pressure between and including 60 psi and 210 psi on tissue positioned between the tissue pad and the blade.

A second embodiment of the invention is for an ultrasonic surgical shears including an ultrasonic surgical blade, a clamping arm, and a tissue pad. The clamping arm is operable to open and close toward the blade. The tissue pad is attached to the clamping arm. The ultrasonic surgical shears also includes a mechanism for limiting a user-applied clamping force on the clamping arm creating an average clamping pressure between and including 60 psi and 210 psi on tissue positioned between the tissue pad and the blade.

Several benefits and advantages are obtained from one or more of the method and the embodiments of the invention. Exerting an ultrasonic surgical shears coaptation pressure from 60 psi to 210 psi provides for improved blood vessel sealing with shorter transection times on 3 mm or smaller blood vessels than conventionally is possible and provides for blood vessel sealing with acceptable transection times and burst pressures on blood vessels larger than 3 mm, which is not conventionally possible.

Applicants experimentally found that applying an ultrasonic surgical shears coaptation pressure ranging from 60 psi to 210 psi (corresponding to a fully-engaged clamping surface area of 0.033 square inches and a clamping force ranging from 2 to 7 pounds) on 4.5 mm to 5 mm diameter blood vessels resulted in successful blood-vessel sealing with transection times of 2 to 4 seconds and with burst pressures of generally 500 to 700 mmHg compared to a transaction time of over 9 seconds and a burst pressure of generally 100 mmHg for a 45 psi clamping pressure (corresponding to a fully-engaged clamping surface area of 0.033 square inches and a clamping force of 1.5 pounds). Applicants also experimentally found that applying an ultrasonic surgical shears coaptation pressure ranging from 120 psi to 180 psi (corresponding to a fully-engaged clamping surface area of 0.033 square inches and a clamping force ranging from 4 to 6 pounds) on 5 mm to 7 mm diameter blood vessels resulted in successful blood-vessel sealing with transection times of 1.5 to 2.0 seconds and with burst pressures of generally 500 mmHg compared to a transaction time of generally 4.5 seconds and a burst pressure of generally 30 mmHg for a 45 psi clamping pressure (corresponding to a fully-engaged clamping surface area of 0.033 square inches and a clamping force of 1.5 pounds).

The present invention has, without limitation, application with straight or curved ultrasonic surgical blades as disclosed in the patents incorporated by reference for use in open or endoscopic procedures as well as in robotic-assisted instruments.

BRIEF DESCRIPTION OF THE FIGURES

FIG. 1 is a block diagram of a method of the invention;

FIG. 3 is a schematic side elevational view of a portion of a second embodiment of an ultrasonic surgical shears of the invention;

FIG. 4 is a cross sectional view of the ultrasonic surgical shears of FIG. 2, taken along lines 4-4 of FIG. 2.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is understood that any one or more of the following-described embodiments, examples, etc. can be combined with any one or more of the other following-described embodiments, examples, etc.

Figure 1:
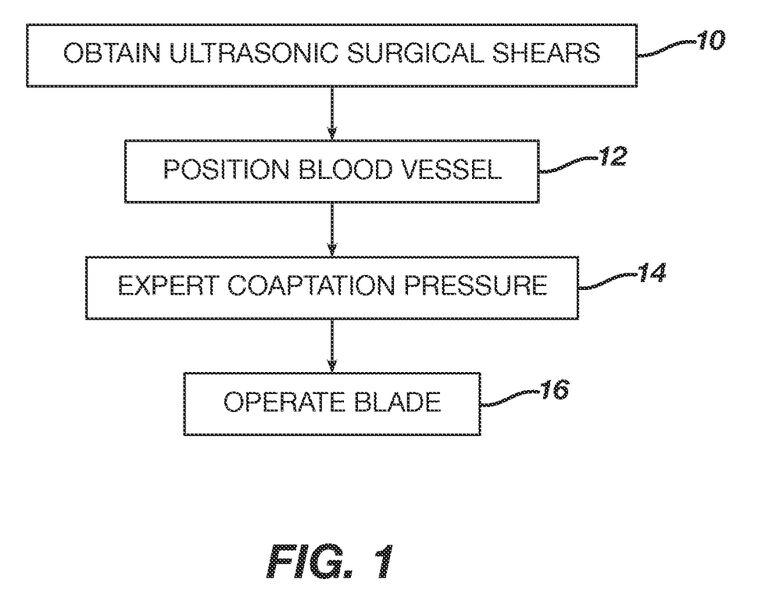
FIG. 1' is an ultrasonic surgical including an elevational view of an ultrasonic generator, a sectioned plan view of an ultrasonic transducer, and a partially sectioned plan view of a clamp coagulator in accordance with the present invention.

Referring now to the Figures, in which like numerals indicate like elements, FIG. 1 illustrates a method of the invention. The method is for sealing a blood vessel of a patient and includes steps a) through d). Step a) is labeled as "Obtain Ultrasonic Surgical Shears" in block 10 of FIG. 1. Step a) includes obtaining an ultrasonic surgical shears including an ultrasonic surgical blade, a clamping arm operable to open and close toward the blade, and a tissue pad attached to the clamping arm. Step b) is labeled as "Position Blood Vessel" in block 12 of FIG. 1. Step b) includes disposing the blood vessel between the blade and the tissue pad. Step c) is labeled as "Exert Coaptation Pressure" in block 14 of FIG. 1. Step c) includes operating the clamping arm to exert an average coaptation pressure on the blood vessel between and including 60 psi and 210 psi. Step d) is labeled as "Operate Blade" in block 16 of FIG. 1. Step d) includes ultrasonically vibrating the blade to transect and seal the blood vessel.

In one illustration of the method of the invention, step b) includes positioning the blade and the clamping arm with the blade and the tissue pad surrounding the blood vessel so that the blood vessel is disposed between the blade and the tissue pad.

In one application of the method of the invention, the average coaptation pressure in step c) is between and including 120 psi and 180 psi. In one variation, the average coaptation pressure in step c) is substantially 150 psi. In one example of the method, the blood vessel has an outside diameter greater than substantially 3 mm. In one variation, the blood vessel has an outside diameter between and including 4.5 mm and 5.0 mm. In another variation, the blood vessel has an outside diameter between and including 5.0 mm and 7.0 mm. In another example, the blood vessel has an outside diameter less than or equal to substantially 3 mm.

FIG. 1' illustrates ultrasonic system 10' comprising an ultrasonic signal generator 15 with ultrasonic transducer 82, hand piece housing 20', and clamp coagulator 120 in accordance with the present invention. Clamp coagulator 120 may be used for open or laparoscopic surgery. The ultrasonic transducer 82, which is known as a "Langevin stack", generally includes a transduction portion 90, a first resonator or end-bell 92, and a second resonator or fore-bell 94, and ancillary components. The ultrasonic transducer 82 is preferably an integral number of one-half system wavelengths ($n\lambda/2$) in length as will be described in more detail later. An acoustic assembly 80 includes the ultrasonic transducer 82, mount 36, velocity transformer 64 and surface 95.

The distal end of end-bell 92 is connected to the proximal end of transduction portion 90, and the proximal end of fore-bell 94 is connected to the distal end of transduction portion 90. Fore-bell 94 and end-bell 92 have a length determined by a number of variables, including the thickness of the transduction portion 90, the density and modulus of elasticity of the material used to manufacture end-bell 92 and fore-bell 94, and the resonant frequency of the ultrasonic transducer 82. The fore-bell 94 may be tapered inwardly from its proximal end to its distal end to amplify the ultrasonic vibration amplitude as velocity transformer 64, or alternately may have no amplification.

The piezoelectric elements 100 may be fabricated from any suitable material, such as, for example, lead zirconate-titanate, lead meta-niobate, lead titanate, or other piezoelectric crystal material. Each of the positive electrodes 96, negative electrodes 98, and piezoelectric elements 100 has a bore extending through the center. The positive and negative electrodes 96 and 98 are electrically coupled to wires 102 and 104, respectively. Wires 102 and 104 are encased within cable 25 and electrically connectable to ultrasonic signal generator 15 of ultrasonic system 10'.

Ultrasonic transducer 82 of the acoustic assembly 80 converts the electrical signal from ultrasonic signal generator 15 into mechanical energy that results in primarily longitudinal vibratory motion of the ultrasonic transducer 82 and an end-effector 180 at ultrasonic frequencies. When the acoustic assembly 80 is energized, a vibratory motion standing wave is generated through the acoustic assembly 80. The amplitude of the vibratory motion at any point along the acoustic assembly 80 depends on the location along the acoustic assembly 80 at which the vibratory motion is measured. A minimum or zero crossing in the vibratory motion standing wave is generally referred to as a node (i.e., where motion is usually minimal), and an absolute value maximum or peak in the standing wave is generally referred to as an anti-node. The distance between an anti-node and its nearest node is one-quarter wavelength ($\lambda/4$).

Wires 102 and 104 transmit the electrical signal from the ultrasonic signal generator 15 to positive electrodes 96 and negative electrodes 98. The piezoelectric elements 100 are energized by an electrical signal supplied from the ultrasonic signal generator 15 in response to a foot switch 118 to produce an acoustic standing wave in the acoustic assembly 80. The electrical signal causes disturbances in the piezoelectric elements 100 in the form of repeated small displacements resulting in large compression forces within the material. The repeated small displacements cause the piezoelectric elements 100 to expand and contract in a continuous manner along the axis of the voltage gradient, producing longitudinal waves of ultrasonic energy. The ultrasonic energy is transmitted through the acoustic assembly 80 to the end-effector 180.

In order for the acoustic assembly 80 to deliver energy to end-effector 180, all components of acoustic assembly 80 must be acoustically coupled to the ultrasonically active portions of clamp coagulator 120. The distal end of the ultrasonic transducer 82 may be acoustically coupled at surface 95 to the proximal end of an ultrasonic waveguide 179 by a threaded connection such as stud 50.

The components of the acoustic assembly 80 are preferably acoustically tuned such that the length of any assembly is an integral number of one-half wavelengths (n$\lambda$/2), where the wavelength $\lambda$, is the wavelength of a preselected or operating longitudinal vibration drive frequency $f_d$ of the acoustic assembly 80, and where n is any positive integer. It is also contemplated that the acoustic assembly 80 may incorporate any suitable arrangement of acoustic elements.

Figure 2:
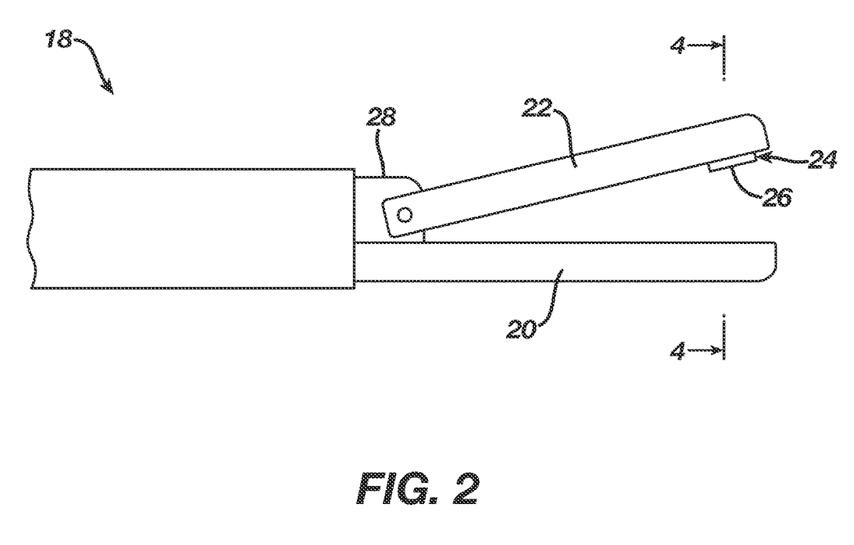
FIG. 2 is a schematic side elevational view of a portion of a first embodiment of an ultrasonic surgical shears of the invention which, in one application, is used to perform the method of FIG. 1.
Figure 2A:
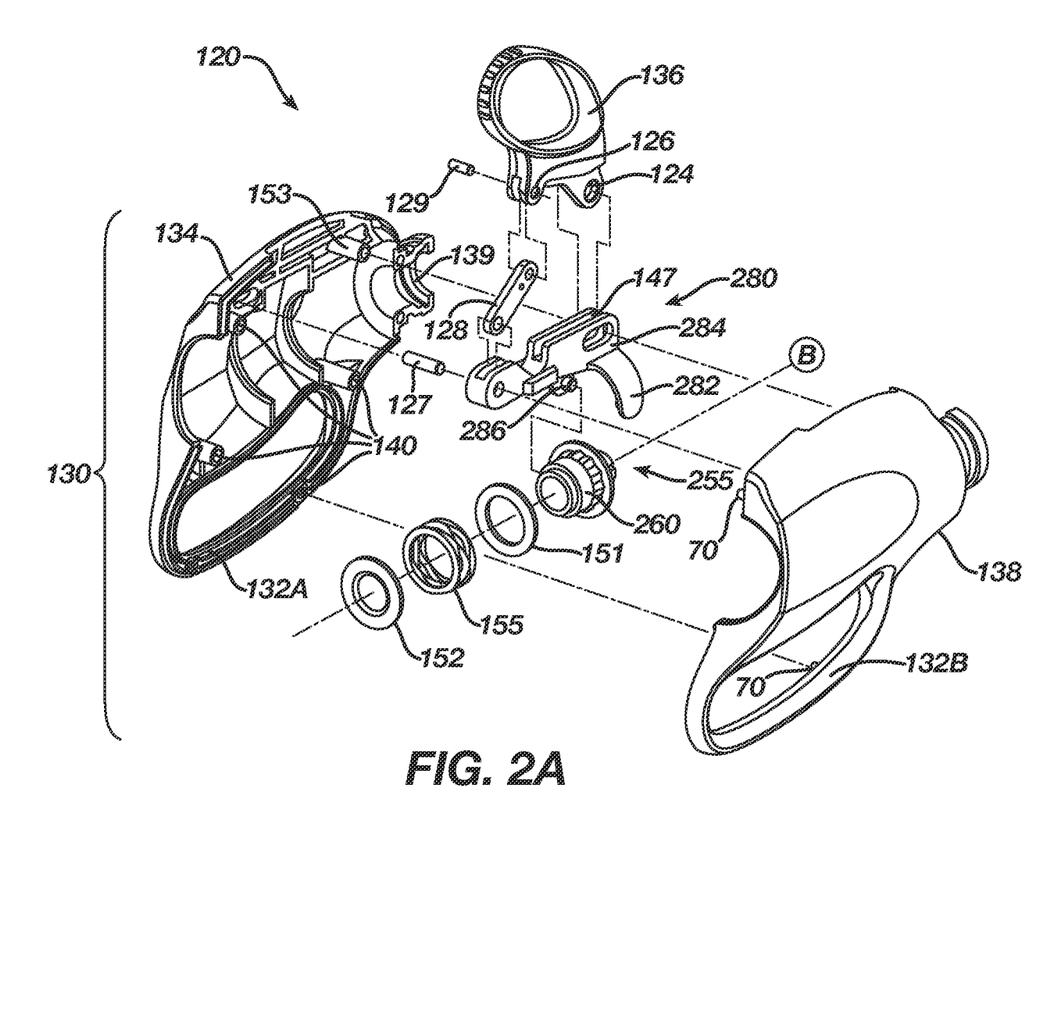
FIG. 2A is an exploded perspective view of a portion of up coagulator in accordance with the present invention.
Figure 2B:
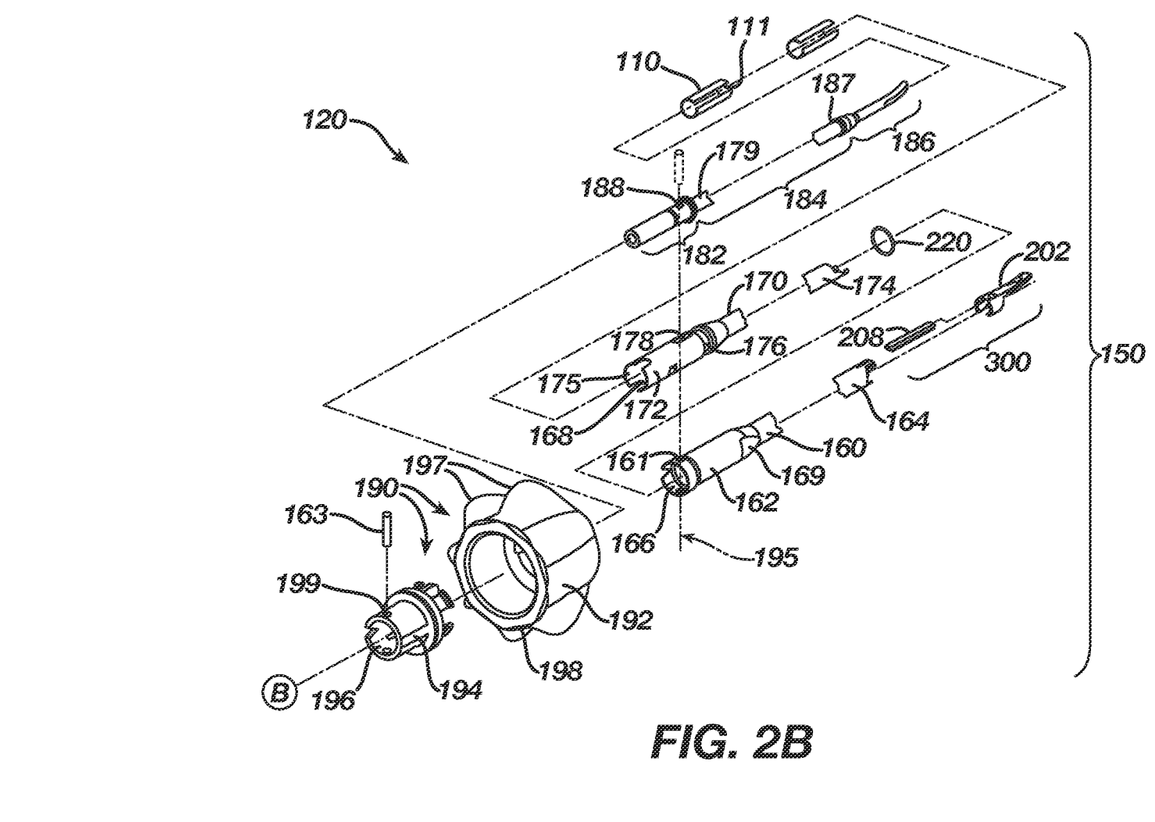
FIG. 2B is an exploded perspective view of a portion of a clamp coagulator in accordance with the present invention.

Referring now to FIGS. 2A and 2B, a clamp coagulator 120 of the surgical system 10' in accordance with the present invention is illustrated. The clamp coagulator 120 is preferably attached to and removed from the acoustic assembly 80 as a unit. The proximal end of the clamp coagulator 120 preferably acoustically couples to the distal surface 95 of the acoustic assembly 80 as shown in FIG. 1. It will be recognized that the clamp coagulator 120 may be coupled to the acoustic assembly 80 by any suitable means.

The clamp coagulator 120 preferably includes an instrument housing 130, and an elongated member 150. The elongated member 150 can be selectively rotated with respect to the instrument housing 130 as further described below. The instrument housing 130 includes a pivoting handle portion 136, and a fixed handle 132A and 132B, coupled to a left shroud 134 and a right shroud 138 respectively.

The right shroud 138 is adapted to snap fit on the left shroud 134. The right shroud 138 is preferably coupled to the left shroud 134 by a plurality of inwardly facing prongs 70 formed on the right shroud 138. The plurality of prongs 70 are arranged for engagement in corresponding holes or apertures 140, which are formed in the left shroud 134. When the left shroud 134 is attached to the right shroud 138, a cavity is formed therebetween to accommodate various components, such as an indexing mechanism 255 as further described below.

The left shroud 134, and the right shroud 138 of the clamp coagulator 120 are preferably fabricated from polycarbonate. It is contemplated that these components may be made from any suitable material without departing from the spirit and scope of the invention.

Indexing mechanism 255 is disposed in the cavity of the instrument housing 130. The indexing mechanism 255 is preferably coupled or attached on inner tube 170 to translate movement of the handle portion 136 to linear motion of the inner tube 170 to open and close the clamp arm assembly 300. When the pivoting handle portion 136 is moved toward the fixed handle portion 130, the indexing mechanism 255 slides the inner tube 170 rearwardly to pivot the clamp arm assembly 300 into a closed position. The movement of the pivoting handle portion 136 in the opposite direction slides the indexing mechanism 255 to displace the inner tube 170 in the opposite direction, i.e., forwardly, and hence pivot the clamp arm assembly 300 into its open position.

The indexing mechanism 255 also provides a ratcheting mechanism to allow the elongated member 150 to rotate about its longitudinal axis relative to instrument housing 130. The rotation of the elongated member 150 enables the clamp arm assembly 300 to be turned to a selected or desired angular position. The indexing mechanism 255 preferably includes a tubular collar 260 and yoke 280.

The tubular collar 260 of the indexing mechanism 255 is preferably snapped onto the proximal end of the inner tube 170 and keyed into opposing openings 168. The tubular collar 260 is preferably fabricated from polyetherimide. It is contemplated that the tubular collar 260 may be constructed from any suitable material.

The pivoting handle portion 136 includes a thumb loop 142, a first hole 124, and a second hole 126. A pivot pin 153 is disposed through first hole 124 of handle portion 136 to allow pivoting as shown by arrow 121 in FIG. 3. As thumb loop 142 of pivoting handle portion 136 is moved in the direction of arrow 121, away from instrument housing 130, a link 128 applies a forward force to yoke 280, causing yoke 280 to move forward. Link 128 is connected to pivoting handle portion 136 by a pin 129, and link 128 is connected to base 284 by a pin 127.

Referring back now to FIG. 2A, yoke 280 generally includes a holding or supporting member 282 and a base 284. The supporting member 282 is preferably semi-circular and has a pair of opposing pawls 286 that extend inwardly to engage with the teeth 269 of the tubular collar 260. It is contemplated that the pawls 286 may be disposed on any suitable part of the yoke 280 for engagement with the teeth 269 of the tubular collar 260 without departing from the spirit and scope of the invention. It will also be recognized that the yoke 280 may have any number of ratchet arms.

The pivoting handle portion 136 preferably is partially disposed in a slot 147 of the base 284 of the yoke 280. The base 284 also includes a base opening 287, an actuator travel stop 290, and a base pin-hole 288. The pivot pin 153 is disposed through the base opening 287. Yoke 280 pawls 286 transfer opening force to inner tube 170 through tubular collar 260, resulting in the opening of clamp arm assembly 300.

The yoke 280 of the clamp coagulator 120 is preferably fabricated from polycarbonate. The yoke 280 may also be made from a variety of materials including other plastics, such as ABS, NYLON, or polyetherimide. It is contemplated that the yoke 280 may be constructed from any suitable material without departing from the spirit and scope of the invention.

Figure 4:
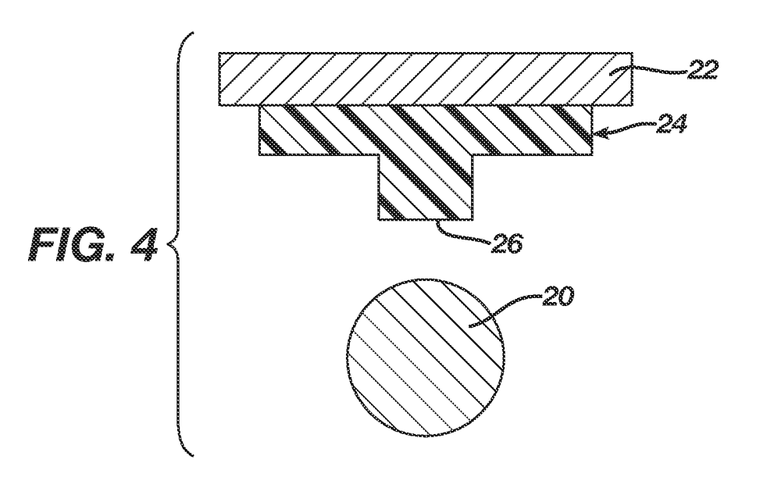
FIG. 4' is a partially sectioned plan view of a clamp coagulator in accordance with the present invention with the clamp arm assembly shown in a closed position.
Figure 5:
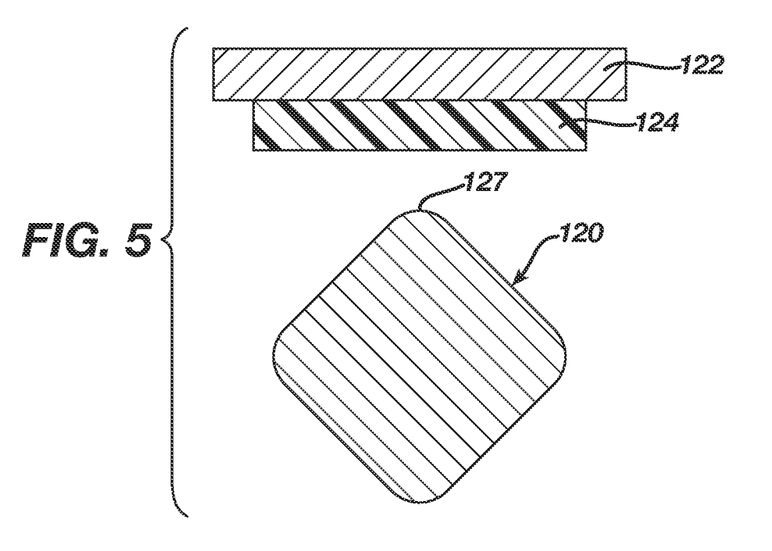
FIG. 5 is a view, as in FIG. 4, but of a different construction of the ultrasonic surgical shears of FIG. 2.

In one exemplary construction employing the method of the invention, as shown in FIG. 4, the blade 20 has a portion which opposes the tissue pad 24 and which has a substantially round transverse cross section, and the tissue pad 24, which is attached to the clamping arm 22, has a substantially "T" shape transverse cross section with the bottom of the "T" defining a clamping surface area 26, the clamping surface area 26 faces substantially toward the blade 20, and step b) disposes the blood vessel between the blade 20 and the clamping surface area 26. In a different construction, as shown in FIG. 5, the blade 120 has a portion which opposes the tissue pad 124 and which has a substantially square transverse cross section with a rounded edge defining a clamping surface area 127, the tissue pad 124, which is attached to the clamping arm 122, has a substantially rectangular transverse cross section, the clamping surface area 127 of the blade 120 faces substantially toward the tissue pad 124, and step b) disposes the blood vessel between the clamping surface area 127 and the tissue pad 124. Other blades, known to those skilled in the art, are equally useful to practice this invention.

In one implementation of the method of the invention, the tissue pad has a clamping surface area of substantially 0.033 square inches. In one variation, step c) exerts a clamping force on the clamping arm between and including 2 pounds and 7 pounds. It is noted that pressure is force per unit area, and that for the same force applied by the clamping arm, the pressure on the engaged portion of a blood vessel that fully engages the entire clamping surface area is less than the pressure on the engaged portion of a blood vessel that, because of smaller diameter, engages only a fraction of the clamping surface area. The pressures discussed herein are pressures seen by tissue when the entire clamping surface area is in contact with the tissue. As previously mentioned, a clamping surface area is the area where the blade and the tissue pad are in close proximity when the clamping arm is in a closed position.

A first embodiment of the invention is for an ultrasonic surgical shears 18 and is shown in FIG. 2. The ultrasonic surgical shears 18 includes an ultrasonic surgical blade 20, a clamping arm 22, and a tissue pad 24. The clamping arm 22 is operable to open and close toward the blade 20. The tissue pad 24 is attached to the clamping arm 22. The ultrasonic surgical shears 18 also includes means 28 for exerting a clamping force on the clamping arm 22 creating a clamping pressure between and including 60 psi and 210 psi on tissue disposed between the tissue pad 24 and the blade 20.

Figure 3:
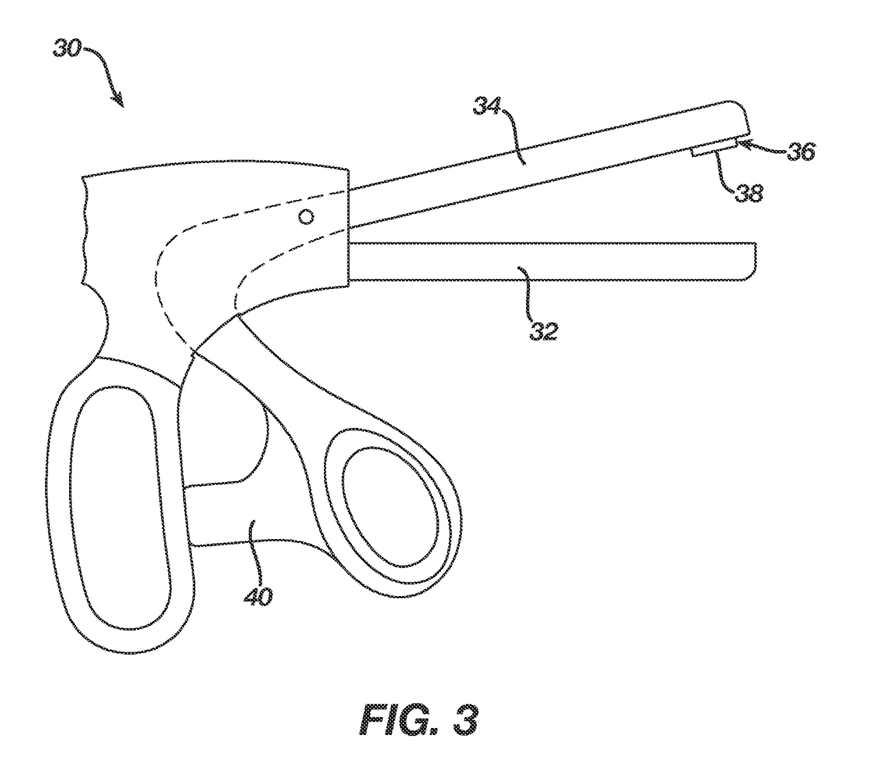
FIG. 3' is a partially sectioned plan view of a clamp coagulator in accordance with the present invention with the clamp arm assembly shown in an open position.

In one enablement of the first embodiment of FIG. 2, the clamping-force-creating means 28 includes a motor which rotates one of the clamping arm and the blade relative to the other of the clamping arm and the blade, wherein the motor is preselected to cause a known-size clamping surface area to exert the desired pressure on tissue large enough to cover the clamping surface area. In another enablement, the clamping-force-creating means 28 includes user-settings to set the value or range of the force or pressure, such settings operating to select a voltage or current to control a variable torque motor to cause a known-size clamping surface to exert the desired pressure or a pressure within a range of desired pressures. In a further enablement, the clamping-force-creating means 28 includes a substantially constant force spring, which applies a predetermined force to the clamping arm. In one variation, the spring is torsional in its application of force. In another variation, the spring is axial in its application of force. It is noted that U.S. Pat. No. 6,325,811 describes one embodiment of a constant force spring design. As illustrated in FIGS. 3' and 4', yoke 280 also transfers a closing force to clamp arm assembly 300 as pivoting handle portion 136 is moved toward instrument housing 130. Actuator travel stop 290 contacts pivot pin 153 at the bottom of the stroke of pivoting handle portion 136, stopping any further movement, or overtravel, of pivoting handle portion 136. Pawls 286 of yoke 280 transfer force to tubular collar 260 through a washer 151, a force limiting spring 155, and collar cap 152. Collar cap 152 is rigidly attached to tubular collar 260 after washer 151 and force limiting spring 155 have been assembled onto tubular collar 260 proximal to enlarged section 262. Thickness of washer 151 may be adjusted during design or manufacturing of clamp coagulator 120 to alter the pre-load of force limiting spring 155. Collar cap 152 is attached to tubular collar 260 by ultrasonic welding, but may alternately be press fit, snap fit or attached with an adhesive. Tubular collar 260, washer 151, force limiting spring 155, and collar cap 152 provide a force limiting feature to clamp arm assembly 300. As pivoting handle portion 136 is moved toward instrument housing 130, clamp arm assembly 300 is rotated toward ultrasonic blade 88. Other equivalent enablements are left to the artisan.

In one application of the first embodiment of FIG. 2, the clamping pressure is between and including 120 psi and 180 psi. In one variation, the clamping pressure is substantially 150 psi. In one implementation of the first embodiment of FIG. 2, the tissue pad 24 has a clamping surface area 26 of substantially 0.033 square inches. In one variation of this implementation, the clamping force on the clamping arm 22 is between and including 2 pounds and 7 pounds.

A second embodiment of the invention is for an ultrasonic surgical shears 30 and is shown in FIG. 3. The ultrasonic surgical shears 30 includes an ultrasonic surgical blade 32, a clamping arm 34, and a tissue pad 36. The clamping arm 34 is operable to open and close toward the blade 32. The tissue pad 36 is attached to the clamping arm 34. The ultrasonic surgical shears 30 also includes means 40 for limiting a user-applied clamping force on the clamping arm 34 creating a clamping pressure between and including 60 psi and 210 psi on tissue disposed between the tissue pad 36 and the blade 32.

In one enablement of the second embodiment of FIG. 3, the force-limitation means 40 includes a torque-limiting mechanism as in a conventional torque wrench. Other equivalent enablements are left to the artisan. Referring to FIGS. 3' and 4', force limiting spring 155 is described in the art as a wave spring, due to the shape of the spring elements 159. It is advantageous to use a wave spring for force limiting spring 155 because it provides a high spring rate in a small physical size well suited to an ultrasonic surgical instrument application where a central area is open for ultrasonic waveguide 179. Force limiting spring 155 is biased between spring surface 158 of collar cap 152 and spring face 165 of washer 151.

In one application of the second embodiment of FIG. 3, the clamping pressure is between and including 120 psi and 180 psi. In one variation, the clamping pressure is substantially 150 psi. In one implementation of the second embodiment of FIG. 3, the tissue pad 36 has a clamping surface area 38 of substantially 0.033 square inches. In one variation of this implementation, the clamping force on the clamping arm is between and including 2 pounds and 7 pounds.

Other embodiments of ultrasonic surgical shears (not shown) which can be used in the method of the invention include, without limitation, those which include a force and/or pressure sensor and a user-sensed indication of the user-applied force and/or pressure measured by the force and/or pressure sensor allowing the user to control the force or pressure. User-sensed indications include, without limitation, a visually-observed value or range on a gauge, a visually-observed value or range on a computer monitor display, a visually observed color or colors, an audibly heard signal or communication, a tactily-felt vibration, etc.

Several benefits and advantages are obtained from one or more of the method and the embodiments of the invention. Exerting an ultrasonic surgical shears coaptation pressure from 60 psi to 210 psi provides for improved blood vessel sealing with shorter transection times on 3 mm or smaller blood vessels than conventionally is possible and provides for blood vessel sealing with acceptable transection times and burst pressures on blood vessels larger than 3 mm, which is not conventionally possible.

Applicants experimentally found that applying an ultrasonic surgical shears coaptation pressure ranging from 60 psi to 210 psi (corresponding to a fully-engaged clamping surface area of 0.033 square inches and a clamping force ranging from 2 to 7 pounds) on 4.5 mm to 5 mm diameter blood vessels resulted in successful blood-vessel sealing with transection times of 2 to 4 seconds and with burst pressures of generally 500 to 700 mmHg compared to a transaction time of over 9 seconds and a burst pressure of generally 100 mmHg for a 45 psi clamping pressure (corresponding to a fully-engaged clamping surface area of 0.033 square inches and a clamping force of 1.5 pounds). Applicants also experimentally found that applying an ultrasonic surgical shears coaptation pressure ranging from 120 psi to 180 psi (corresponding to a fully-engaged clamping surface area of 0.033 square inches and a clamping force ranging from 4 to 6 pounds) on 5 mm to 7 mm diameter blood vessels resulted in successful blood-vessel sealing with transection times of 1.5 to 2.0 seconds and with burst pressures of generally 500 mmHg compared to a transaction time of generally 4.5 seconds and a burst pressure of generally 30 mmHg for a 45 psi clamping pressure (corresponding to a fully-engaged clamping surface area of 0.033 square inches and a clamping force of 1.5 pounds).

While the present invention has been illustrated by a description of several embodiments and a method, it is not the intention of the applicants to restrict or limit the spirit and scope of the appended claims to such detail. Numerous other variations, changes, and substitutions will occur to those skilled in the art without departing from the scope of the invention. For instance, the ultrasonic surgical shears and the method for sealing a blood vessel of the invention have application in robotic assisted surgery taking into account the obvious modifications of such systems, components and methods to be compatible with such a robotic system. It will be understood that the foregoing description is provided by way of example, and that other modifications may occur to those skilled in the art without departing from the scope and spirit of the appended Claims.

What is claimed is:

1. An ultrasonic surgical shears comprising:
   a) an ultrasonic surgical blade;
   b) a clamping arm operable to open and close toward the blade;
   c) a tissue pad attached to the clamping arm; and
   d) a force limiting spring for transferring a predetermined clamping force, wherein the blade and tissue pad define a clamping surface area wherein the force limiting spring limits the predetermined clamping force to provide for an average clamping pressure between and including 120 psi and 210 psi at the clamping surface area.

2. The ultrasonic surgical shears of claim 1, wherein the average clamping pressure is between and including 120 psi and 180 psi.

3. The ultrasonic surgical shears of claim 1, wherein the force limiting spring is pre-loaded.

4. The ultrasonic surgical shears of claim 1, wherein the force limiting spring is a wave spring.

5. An ultrasonic surgical shears comprising:
   a) an ultrasonic surgical blade;
   b) a clamping arm operable to open and close toward the blade;
   c) a tissue pad attached to the clamping arm; and
   d) a force limiting spring for transferring a clamping force, wherein the blade and tissue pad define a clamping surface area wherein the clamping force provides an average clamping pressure between and including 120 psi and 210 psi at the clamping surface area.

6. An ultrasonic surgical shears comprising:
   a) an ultrasonic surgical blade;
   b) a clamping arm operable to open and close toward the blade;
   c) a tissue pad attached to the clamping arm; and
   d) a force limiting spring for transferring a predetermined minimum clamping force and a predetermined maximum clamping force, wherein the blade and tissue pad define a clamping surface area wherein the predetermined minimum clamping force provides for an average clamping pressure no less than 120 psi at the clamping surface area and the predetermined maximum clamping force provides for an average clamping pressure no greater than 210 psi at the clamping surface area.

7. An ultrasonic surgical shears comprising:
   a) an ultrasonic surgical blade;
   b) a clamping arm operable to open and close toward the blade;
   c) a tissue pad attached to the clamping arm;
   d) a handle assembly including a trigger moveably connected to the handle assembly; and
   d) a spring
   wherein the trigger is operatively connected to the clamp arm such that movement of the trigger from a first position to a second position causes the clamping arm to move from an open position to a closed position against the blade, wherein the blade and tissue pad define a clamping surface area in the closed position, and the spring transfers a clamping force when the trigger is at the second position, such that the predetermined clamping force provides for an average clamping pressure no less than 120 psi and no greater than 210 psi at the clamping surface area.

8. The ultrasonic surgical shears of claim 7, wherein the handle assembly further includes a trigger motion stop feature, which prevents movement of the trigger beyond the second position.

9. The ultrasonic surgical shears of claim 7, wherein the spring is pre-loaded.

10. An ultrasonic surgical shears comprising:
    a) an ultrasonic surgical blade;
    b) a clamping arm operable to open and close toward the blade;
    c) a tissue pad attached to the clamping arm;
    d) a handle assembly including a trigger moveably connected to the handle assembly and a trigger motion stop feature; and
    d) a spring
    wherein the trigger is operatively connected to the clamp arm such that movement of the trigger from a first position to a second position causes the clamping arm to move from an open position to a closed position against the blade, wherein the blade and tissue pad define a clamping surface area in the closed position, and the spring transfers a predetermined clamping force when the trigger is at the second position, such that the predetermined clamping force provides for an average clamping pressure no less than 120 psi and the trigger motion stop feature limits the predetermined clamping force to no greater than 210 psi at the clamping surface area.

11. An ultrasonic surgical shears comprising:
a) an ultrasonic surgical blade;
b) a clamping arm operable to open and close toward the blade;
c) a tissue pad attached to the clamping arm;
d) a handle assembly including a trigger moveably connected to the handle assembly and a trigger motion stop feature; and
d) a spring
wherein the trigger is operatively connected to the clamp arm such that movement of the trigger from a first position to a second position causes the clamping arm to move from an open position to a closed position against the blade, wherein the blade and tissue pad define a clamping surface area in the closed position, and the spring transfers a predetermined clamping force when the trigger is at the second position, such that the trigger motion stop feature limits the predetermined clamping force to no greater than 210 psi at the clamping surface area.

12. An ultrasonic surgical shears comprising:
a) an ultrasonic surgical blade;
b) a clamping arm operable to open and close toward the blade;
c) a tissue pad attached to the clamping arm; and
d) a force limiting spring for providing a predetermined clamping force, wherein the blade and tissue pad define a clamping surface area wherein the predetermined clamping force provides an average clamping pressure between and including 120 psi and 210 psi at the clamping surface area.

* * * * *